(12) United States Patent
Zhong

(10) Patent No.: US 8,425,432 B2
(45) Date of Patent: Apr. 23, 2013

(54) RECONFIGURABLE INTEGRATED LANCET SYSTEM

(75) Inventor: Weiping Zhong, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 1004 days.

(21) Appl. No.: 11/919,835

(22) PCT Filed: May 4, 2006

(86) PCT No.: PCT/US2006/017460
§ 371 (c)(1),
(2), (4) Date: Nov. 2, 2007

(87) PCT Pub. No.: WO2006/121884
PCT Pub. Date: Nov. 16, 2006

(65) Prior Publication Data
US 2009/0093831 A1    Apr. 9, 2009

Related U.S. Application Data
(60) Provisional application No. 60/678,024, filed on May 5, 2005.

(51) Int. Cl.
*A61B 5/00* (2006.01)

(52) U.S. Cl.
USPC ........................................................ 600/583

(58) Field of Classification Search .......... 600/562–584; 606/167, 181–183
See application file for complete search history.

(56) References Cited

U.S. PATENT DOCUMENTS

| | | | |
|---|---|---|---|
| 4,637,403 A | 1/1987 | Garcia et al. | 128/770 |
| 4,924,879 A | 5/1990 | O'Brien | 128/770 |
| 5,029,583 A | 7/1991 | Meserol et al. | 128/633 |
| 5,279,294 A | 1/1994 | Anderson et al. | 128/633 |
| 5,324,303 A | 6/1994 | Strong et al. | 606/181 |
| 5,871,494 A | 2/1999 | Simons et al. | 606/181 |
| 6,379,317 B1 | 4/2002 | Kintzig et al. | 600/573 |
| 2004/0267229 A1 | 12/2004 | Moerman et al. | 604/500 |

FOREIGN PATENT DOCUMENTS

| | | |
|---|---|---|
| WO | WO 97/42882 | 11/1997 |
| WO | WO 03/015627 A2 | 2/2003 |

OTHER PUBLICATIONS

Written Opinion corresponding to International Patent Application Serial No. PCT/US2006/017460, European Patent Office, dated Aug. 11, 2006, 5 pages.

International Search Report corresponding to International Patent Application Serial No. PCT/US2006/017460, European Patent Office, dated Aug. 11, 2006, 3 pages.

*Primary Examiner* — Max Hindenburg
(74) *Attorney, Agent, or Firm* — Nixon Peabody LLP

(57) ABSTRACT

A reconfigurable integrated lancet system comprises a testing device having a housing, a lancet holding device frame, a lancet, and at least one connection mechanism. The lancet holding device frame is adapted to fasten around a periphery of the housing of the testing device. The lancet holding device frame has a first lock receiving region. The lancet has a second lock receiving region. The at least one connection mechanism has a first locking end and a second locking end. The first locking end is adapted to interact within the first lock receiving region of the lancet holding device frame, to connect the connection mechanism to the lancet holding device frame. The second locking end is adapted to interact within the second lock receiving region of the lancet, to connect the connection mechanism to the lancet.

10 Claims, 8 Drawing Sheets

RECONFIGURABLE INTEGRATED LANCET SYSTEM

CROSS-REFERENCE TO RELATED APPLICATIONS

This application claims priority to Application No. 60/678,024 filed on May 5, 2005, which is incorporated by reference in its entirety.

FIELD OF THE INVENTION

The present invention relates generally to a fluid-monitoring system and, more particularly, to reconfigurable integrated lancet system to be used with a meter or instrument for handling at least one sensor that used in analyzing at least one analyte in a fluid contained therein (e.g., blood glucose, cholesterol).

BACKGROUND OF THE INVENTION

People suffering from various forms of diabetes and other diseases routinely need to test a liquid sample, such as blood, in order to determine the level of an analyte, such as glucose, within the liquid sample. The results of such tests can be used to determine what, if any, insulin or other medication needs to be administered. In one type of blood glucose testing system, sensors are used to test a sample of blood.

To generate a sample to be tested a user typically uses a lancet having a sharp end to penetrate the user's skin. A liquid sample then forms near the area lanced. The liquid sample is then collected and placed on a test strip. The test strip is typically placed within a test meter and the analyte level is measured. In some devices the test strip is inserted into the testing device after the sample has been collected on the test strip, while in other embodiments the test strip is within the testing device prior to the collection of the sample. As a user typically needs to perform several tests a day, the user normally carries testing supplies with them. Requiring the user to carry all of these components separately can be inconvenient.

Therefore, several attempts have been made to integrate all of these components into one device. One of these prior attempts involves the attempt to integrate as many of these components into a single component as possible such as by combining a lancet into a housing of the testing device in a manner that the lancet is permanently affixed to the testing device. Another prior attempt involves designing the housing of the testing device so that the lancet may be removably attached to the housing of the testing device. While these attempts allow a user to have a testing device with an integrated lancet if they purchase an entirely new device, many users may not find it practicable to replace a working testing device, or may not have the financial resources to purchase a new testing device. Therefore, it would be desirable to allow a user to attach an existing lancet to an existing testing device without the need to purchase a new testing device.

SUMMARY OF THE INVENTION

According to one embodiment of the present invention, a reconfigurable integrated lancet system comprises a testing device with a housing, a lancet holding device frame, a lancet, and at least one connection mechanism. The lancet holding device frame is adapted to fasten around a periphery of the housing of the testing device. The lancet holding device has a first lock receiving region. The lancet has a second lock receiving region. The at least one connection mechanism has a first locking end and a second locking end. The first locking end is adapted to interact within the first locking receiving region of the lancet holding device frame to connect the connection mechanism to the lancet holding device frame. The second locking end is adapted to interact within the second lock receiving region of the lancet to connect the connection mechanism to the lancet.

According to another embodiment of the present invention, a reconfigurable integrated lancet system comprises a testing device with a housing, a lancet holding device frame, a lancet, and a connecting arm. The lancet holding device frame has a plurality of securing clips adapted to fasten around a portion of a periphery of the housing of the testing device to secure the lancet holding device frame to the testing device. The connecting arm has an arm region and a fastening region. The arm region is adapted to fasten the connecting arm to the lancet holding device frame. The fastening region is adapted to fasten around a portion of the periphery of the housing of the lancet to secure the lancet to the connecting arm.

According to a further embodiment of the present invention, a reconfigurable integrated lancet system comprises a testing device with a housing having a front surface and a rear surface, a flexible lancet holding device frame, a lancet with a first lock receiving region, and at least one connection element. The flexible lancet holding device frame is adapted to fasten around a periphery of the housing of the testing device. The lancet holding device frame has a first securing strap and a second securing strap. The first securing strap is adapted to cover a portion of the front surface of the testing device. The second securing strap is adapted to cover a portion of the rear surface of the testing device. The at least one connection element has at least a first locking end. The first locking end is adapted to interact within the first lock receiving region of the lancet to connect the connection element to the lancet.

The above summary of the present invention is not intended to represent each embodiment, or every aspect, of the present invention. Additional features and benefits of the present invention are apparent from the detailed description and figures set forth below.

DESCRIPTION OF ILLUSTRATED EMBODIMENTS

Figure 1:
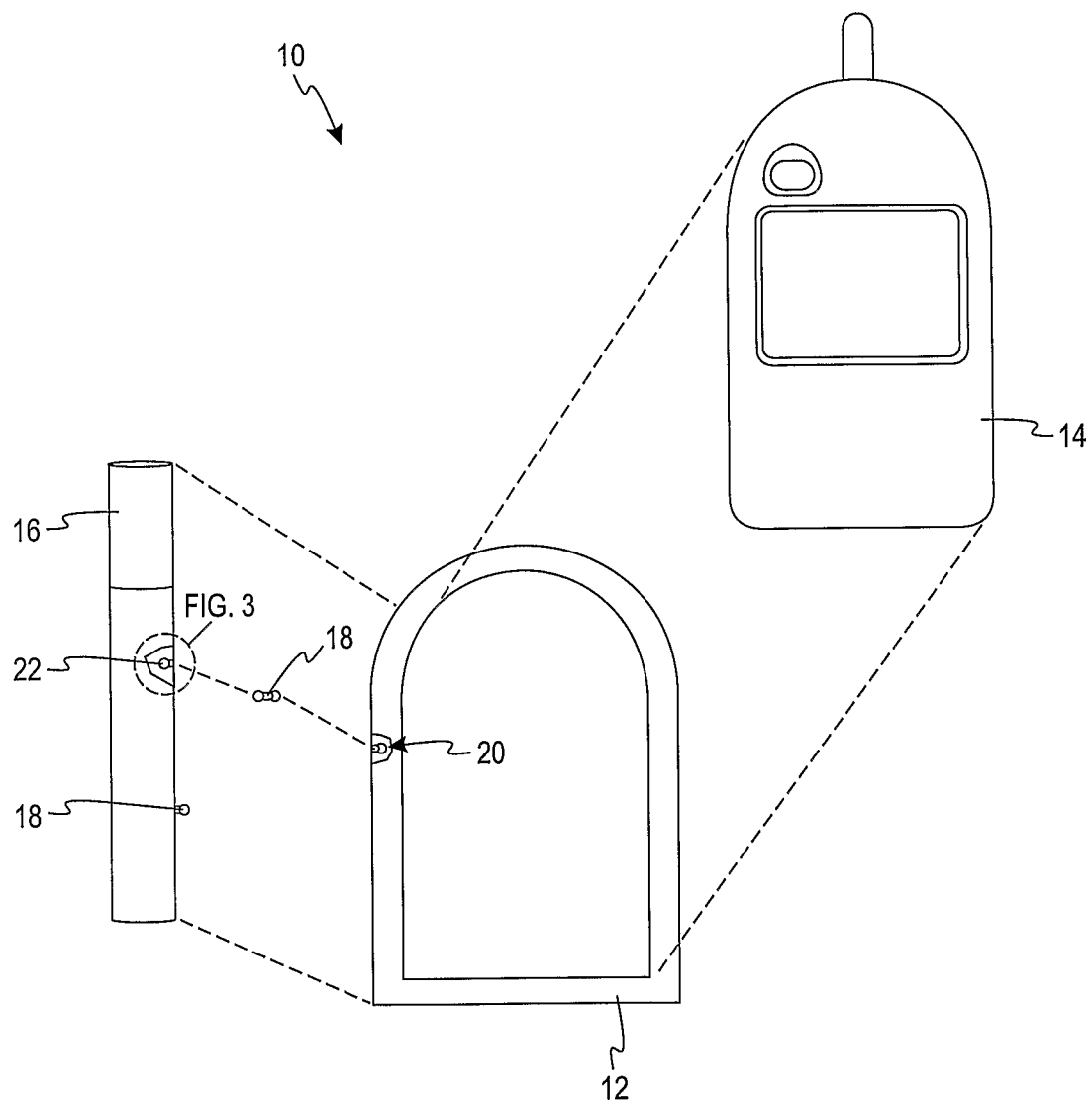
FIG. 1 is an exploded perspective view of the component parts of an integrated lancet system according to one embodiment of the present invention.

Referring now to FIG. 1, an exploded view of the component parts of a reconfigurable integrated lancet system 10 comprise a lancet holding device frame 12 that is adapted to attach to a testing device 14. The lancet holding device frame 12 is further adapted to secure a lancet 16. The lancet holding device frame 12 is manufactured from a molded polymeric material. It is further contemplated that a lancet holding device frame may be manufactured from a rubber material, a metallic material, or any other flexible or malleable material. The lancet holding device frame 12 is adapted to fasten around a periphery of the testing device 14, such that the frame 12 is secured to the testing device 14. The use of a molded polymeric material allows the lancet holding device frame 12 to be semi-rigid to increase the strength of the frame 12. At least one connection mechanism 18 attaches the lancet 16 to the lancet holding device frame 12.

Figure 3:
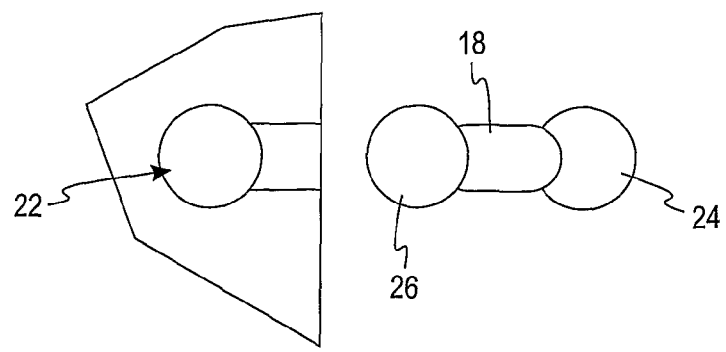
FIG. 3 is an enlarged partial view of a connection mechanism used in the integrated lancet system according to the embodiment of FIG. 1.

As shown in FIG. 1, two connection mechanisms 18 are utilized. The connection mechanisms have a first locking end 24 and a second locking end 26. The first locking end 24 is adapted to fit within a first lock receiving region 20 of the lancet holding device frame 12. The second locking end is adapted to fit within a second lock receiving region 22 (FIG. 3) of the lancet 16. As shown in FIGS. 1 and 3, the connection mechanism 18 is fully removable from both the lancet holding device frame 12 and the lancet 16. The first and second locking ends 24, 26 are slightly deformable to assist in fitting within the first and second lock receiving regions 20, 22.

According to an alternate embodiment of the present invention, the at least one connection mechanism may be integrated within either the lancet or the lancet holding device frame. In such an embodiment the connection mechanism is fixedly connected to the lancet or the lancet holding device frame, while still allowing the lancet to be removably attached to the lancet holding device frame.

Figure 2:
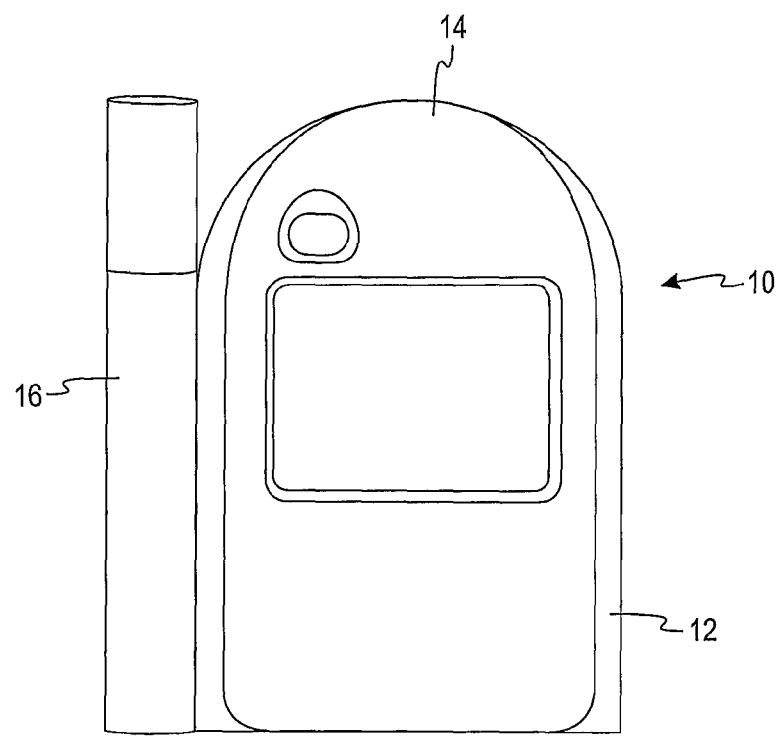
FIG. 2 is a perspective view of the integrated lancet system according to the embodiment of FIG. 1.

FIG. 2 shows the components of the integrated lancet system 10 in an assembled state. The lancet 16 is attached to the lancet holding device frame 12 that is secured to the testing device 14. Such an integrated lancet system 10 allows a user to more easily keep track of the lancet 16, as it is attached to the testing device 14.

To utilize the embodiment of the present invention depicted in FIGS. 1-3, the user fastens the lancet holding device frame 12 around the testing device 14. The lancet holding device frame 12 is shaped so that it securely attaches to an outer periphery of a housing of the testing device 14. The at least one connection mechanism 18 is attached to the lancet holding device frame 12. It is contemplated that the connection mechanism 18 may be attached to the lancet holding device frame 12 prior to fastening the frame 12 to the testing device 14. It is further contemplated that the connection mechanism 18 may be attached to the lancet holding device frame 12 after fastening the frame 12 to the testing device 14. The lancet 16 is positioned such that the second lock receiving region 22 may interact with the connection mechanism 18 to attach the lancet 16 to the lancet holding device frame 12.

Figure 4:
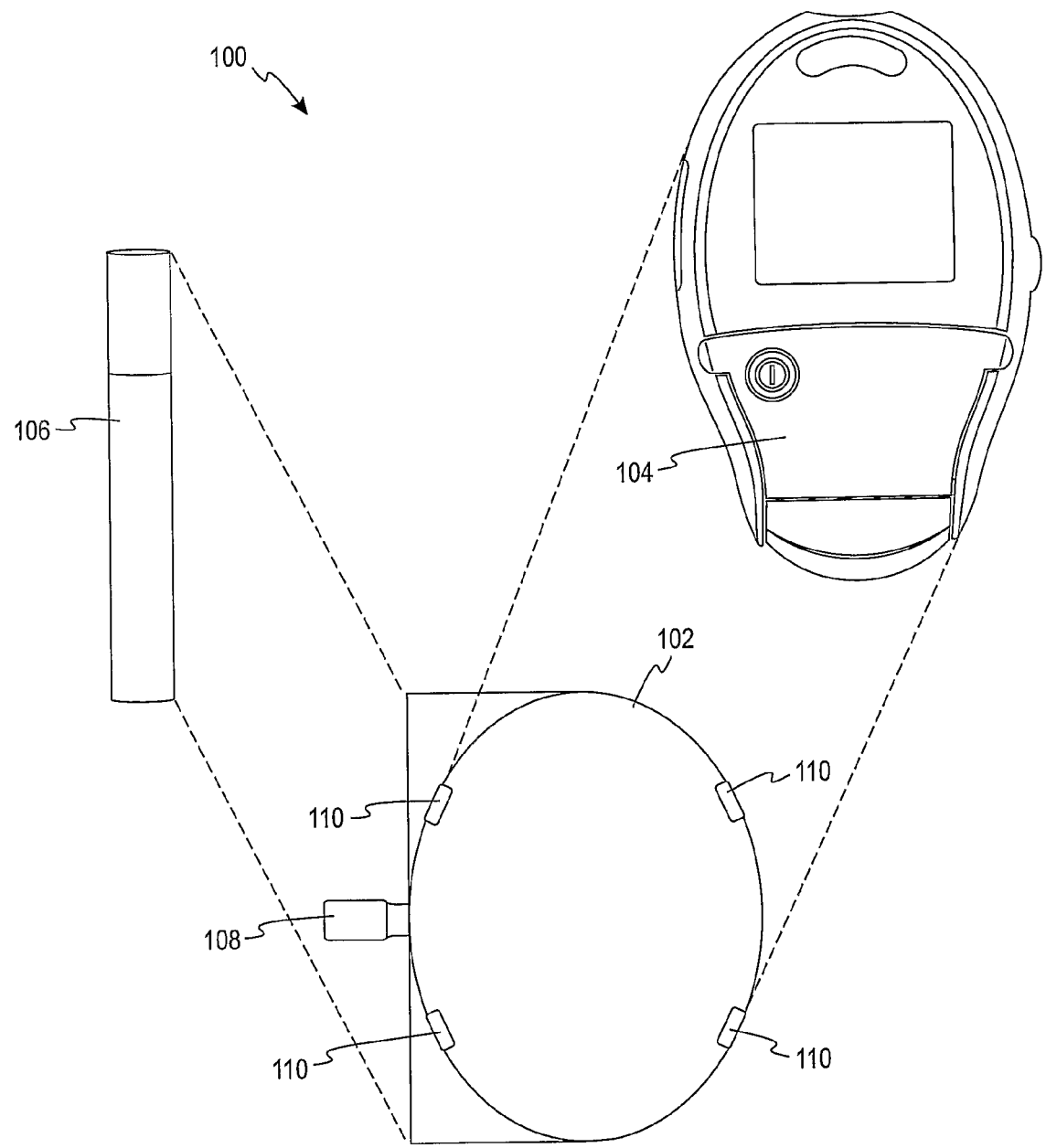
FIG. 4 is an exploded perspective view of the component parts of an integrated lancet system according to another embodiment of the present invention.

Turning next to FIG. 4, an exploded view of another embodiment of a reconfigurable integrated lancet system 100 is shown. The integrated lancet system 100 comprises a lancet holding device frame 102, a prior art testing device 104, and a lancet 106. The lancet holding device frame 102 is manufactured from a molded polymeric material according to one embodiment of the present invention. It is further contemplated that a lancet holding device frame may be manufactured from a rubber material, a metallic material, or any other flexible or malleable material. The lancet holding device frame 102 has a plurality of securing clips 110 that are adapted to fit around a portion of an outer housing of the testing device 104 to secure the frame 102 to the testing device 104. The lancet holding device frame has four securing clips 110 as disclosed in FIG. 4, however, the number of securing clips 110 used may vary based on the geometry of the testing device 104.

Figure 6:
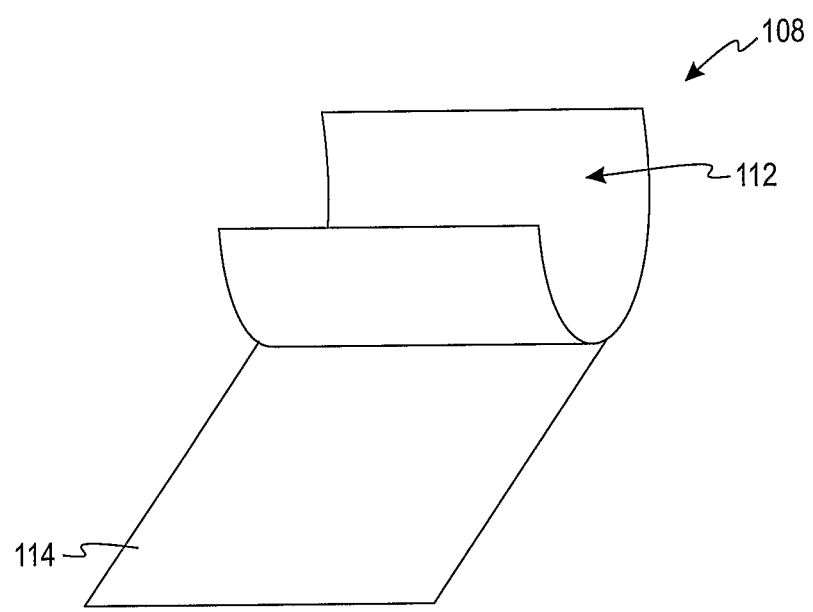
FIG. 6 is an enlarged partial perspective view of a connection mechanism used in the integrated lancet system according to the embodiment of FIG. 4.

A connecting arm 108 is attached to the lancet holding device frame 102. The connecting arm 108 is adapted to secure the lancet 106. As shown in FIG. 6, the connecting arm 108 has an arm region 114 and a generally U-shaped fastening region 112. The arm region 114 is adapted to secure the connecting arm 108 to the lancet holding device frame 102. The arm region 114 may be secured to the lancet holding device frame 102 via a mechanical fastener, an adhesive, an ultrasonic weld, or other fastening techniques. It is further contemplated that in an alternative embodiment the arm region may be integrally formed into the lancet holding device frame, such that the connecting arm is a part of the lancet holding device frame. The U-shaped fastening region 112 is adapted to fit around a portion of a periphery of the lancet 106. In this manner the lancet 106 is secured within the connecting arm.

Figure 5:
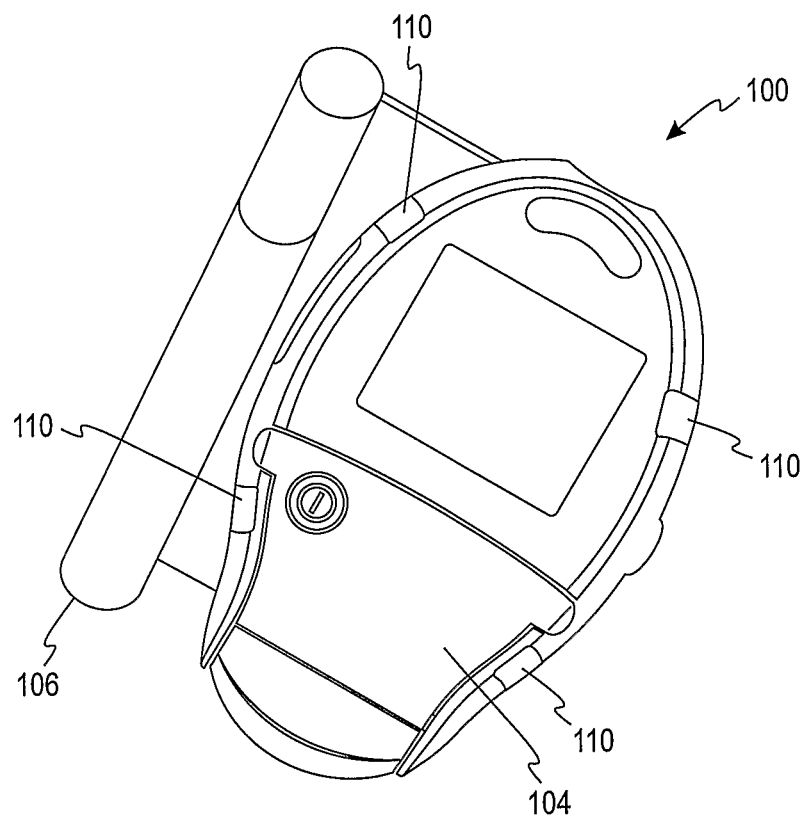
FIG. 5 is a perspective view of the integrated lancet system according to the embodiment of FIG. 4.

FIG. 5 shows the components of the integrated lancet system 100 in an assembled state. The lancet 106 attaches to the lancet holding device frame 102 via the connecting arm 108. The lancet holding device frame attaches to the testing device 104, thus allowing a user to form an integrated lancet system 100 with a testing device 104.

To utilize the embodiment of the present invention depicted in FIGS. 4-6, the user fastens the lancet holding device frame 102 to the testing device 104 via the plurality of securing clips 110. The generally U-shaped region 112 of the connecting arm 108 secures the lancet 106 to the connecting arm. The connecting arm 108 attaches to the lancet holding device frame 102 via the arm region 104.

Figure 7:
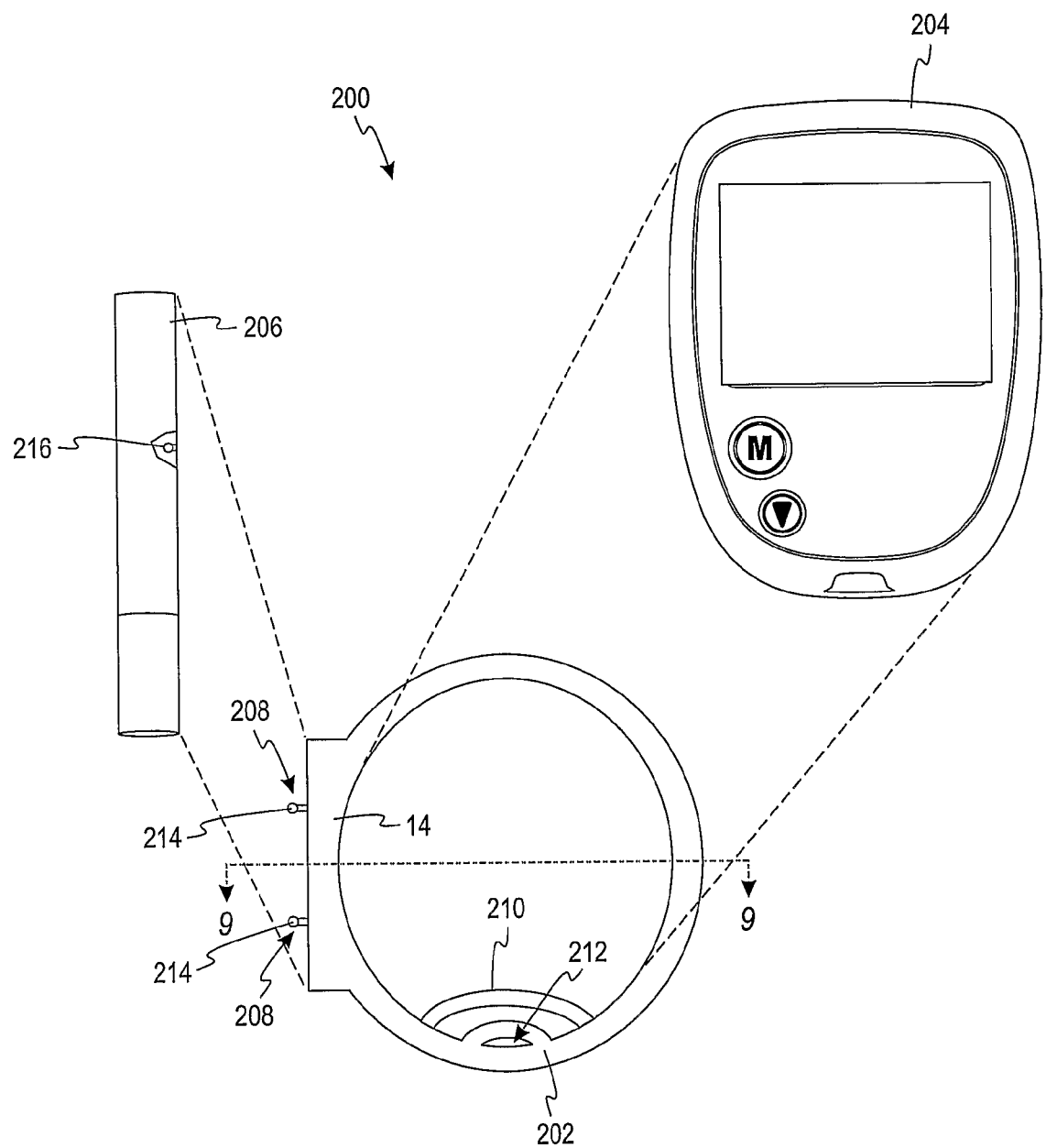
FIG. 7 is an exploded perspective view of the component parts of an integrated lancet system according to a further embodiment of the present invention.

Referring next to FIG. 7, an exploded view of a further embodiment of a reconfigurable integrated lancet system 200. The integrated lancet system 200 comprises a flexible lancet holding device frame 202, a prior art testing device 204, and a lancet 206. The lancet holding device frame 202 is manufactured from a flexible material, such as rubber, or a flexible polymeric material. The lancet holding device frame 202 is adapted to stretch around a periphery of the testing device 204 to secure the lancet holding device frame 202 to the testing device 204. To secure the lancet holding device frame 202 to a front surface and a rear surface of a housing of the testing device 204, a front securing strap 210 and a similar rear securing strap (not shown) are utilized. The front securing strap 210 helps to inhibit or prevent the lancet holding device 202 from sliding off of the housing of the testing device 204 towards the rear of the testing device 204. Similarly, the rear securing strap helps to inhibit or prevent the lancet holding device from sliding off of the housing of the testing device 204 towards the front of the testing device 204.

In addition to the front and rear securing straps, the lancet holding device frame 202 desirably has a sensor pass-through region 212. The sensor pass-through region 212 is adapted to allow a test sensor to be placed into and removed from the testing device 204 with the lancet holding device frame 202 remaining in place.

Figure 9:
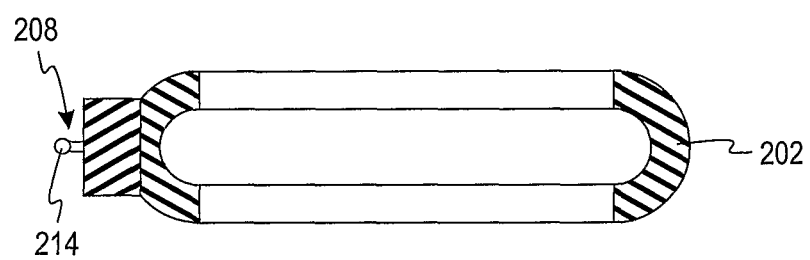
FIG. 9 is cross-sectional view of a lancet holding device frame taken generally through line 9-9 of FIG. 7.

As can be seen in FIG. 9, the cross section of the lancet holding device frame 202 is adapted to envelope the periphery of the housing of a testing device. The flexible lancet holding device frame 202 is adapted to be from about 95% to about 99% as large as the testing device that it will be used with in its natural state, but the flexible material allows the lancet holding device frame 202 to be stretched over the periphery of the testing device.

The lancet holding device frame 202 further has at least one connection element 208 adapted to connect the lancet 206 to the lancet holding device frame 202. The connection element 208 has a first locking end 214, adapted to fit within a first lock receiving region 216 of the lancet 206, similar to that previously described in relation to FIGS. 1-3.

Figure 8:
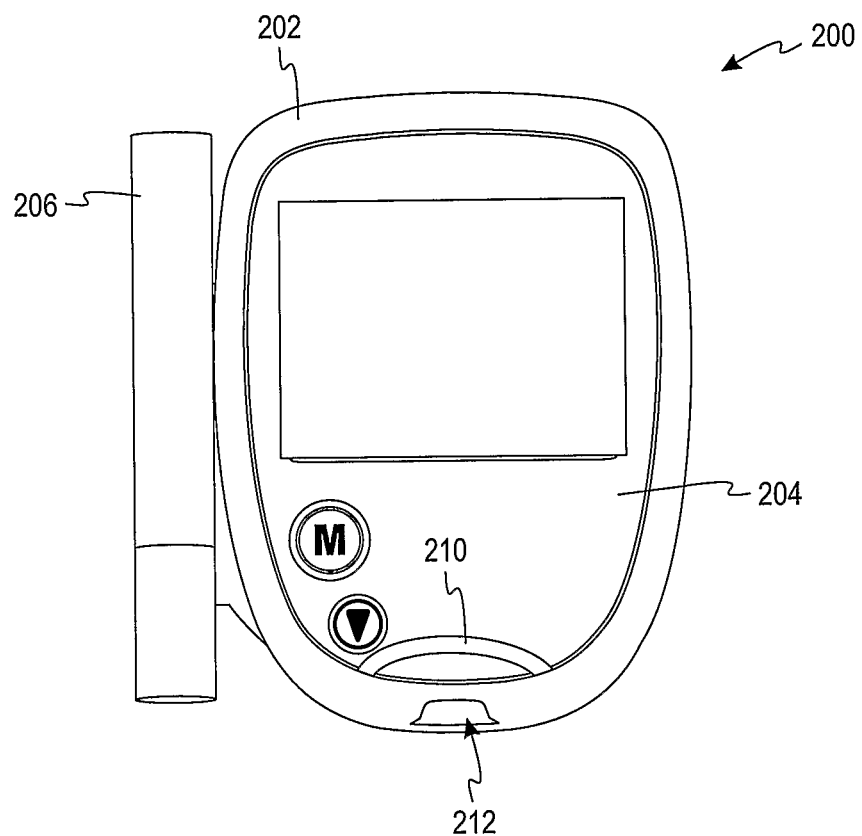
FIG. 8 is a perspective view of the integrated lancet system according to the embodiment of FIG. 7.

The assembled reconfigurable integrated lancet system 200 is shown in FIG. 8. The lancet 206 is attached to the flexible lancet holding device frame 202 that is secured around the periphery of the testing device 204. The front securing strap 210 helps to inhibit or prevent the lancet holding device frame 202 from sliding off the rear of the testing device 204. Similarly, a rear securing strap (not shown) helps to inhibit or prevent the lancet holding device frame 202 from sliding off of the front of the testing device 204. Additionally, the sensor pass-through region 212 of the flexible lancet holding device frame 202 is positioned in the assembled integrated lancet system 200 to allow a test sensor to enter the testing device 204.

To utilize the embodiment of the present invention depicted in FIGS. 7-9, the user initially places the flexible lancet holding device frame 202 around the periphery of the testing device 204. The front securing strap 210 and the rear securing strap (not shown) assist in securing the lancet holding device frame 202, helping to inhibit or prevent the frame 202 from moving off of the front or the rear of the testing device 204. The at least one connection element 208 is placed within the first lock receiving region 216 of the lancet 206. Thus, a reconfigurable integrated lancet system 200 is formed.

Alternative Embodiment A

A reconfigurable integrated lancet system comprising:
a testing device having a housing;
a lancet holding device frame adapted to fasten around a periphery of the housing of the testing device, the lancet holding device frame having a first lock receiving region;
a lancet having a second lock receiving region; and
at least one connection mechanism having a first locking end and a second locking end, the first locking end adapted to interact within the first lock receiving region of the lancet holding device frame to connect the connection mechanism to the lancet holding device frame, the second locking end adapted to interact within the second lock receiving region of the lancet to connect the connection mechanism to the lancet.

Alternative Embodiment B

The reconfigurable integrated lancet system of Alternate Embodiment A wherein the at least one connection mechanism is releasably connected to the lancet holding device frame.

Alternative Embodiment C

The reconfigurable integrated lancet system of Alternate Embodiment A wherein the connection mechanism is releasably connected to the lancet.

Alternative Embodiment D

The reconfigurable integrated lancet system of Alternate Embodiment A wherein the connection mechanism is fixedly connected to the lancet holding device frame.

Alternative Embodiment E

The reconfigurable integrated lancet system of Alternate Embodiment A wherein the connection mechanism is fixedly connected to the lancet.

Alternative Embodiment F

The reconfigurable integrated lancet system of Alternate Embodiment A wherein the lancet holding device frame is a rigid polymeric material.

Alternative Embodiment G

A reconfigurable integrated lancet system comprising:
a testing device having a housing;
a lancet holding device frame having a plurality of securing clips adapted to fasten around a portion of a periphery of the housing of the testing device to secure the lancet holding device frame to the testing device;
a lancet; and
a connecting arm having an arm region and a fastening region, the arm region adapted to fasten the connecting arm to the lancet holding device frame, the fastening region adapted to fasten around a portion of a periphery of the lancet to secure the lancet to the connecting arm.

Alternative Embodiment H

The reconfigurable integrated lancet system of Alternate Embodiment G wherein a mechanical fastener fastens the arm region of the connecting arm to the lancet holding device frame.

Alternative Embodiment I

The reconfigurable integrated lancet system of Alternate Embodiment G wherein an adhesive fastens the arm region of the connecting arm to the lancet holding device frame.

Alternative Embodiment J

The reconfigurable integrated lancet system of Alternate Embodiment G wherein an ultrasonic weld fastens the connecting arm to the lancet holding device frame.

Alternative Embodiment K

The reconfigurable integrated lancet system of Alternate Embodiment G wherein the arm region of the connecting arm is integrally formed into the lancet holding device frame.

Alternative Embodiment L

The reconfigurable integrated lancet system of Alternate Embodiment G wherein the fastening region of the connecting arm is generally U-shaped.

Alternative Embodiment M

The reconfigurable integrated lancet system of Alternate Embodiment G wherein the lancet holding device frame is a rigid polymeric material.

Alternative Embodiment N

A reconfigurable integrated lancet system comprising:
a testing device having a housing with a front surface and a rear surface;
a flexible lancet holding device frame adapted to fasten around a periphery of the housing of the testing device, the lancet holding device frame having a first securing strap and a second securing strap, the first securing strap being adapted to cover a portion of the front surface of the testing device, the second securing strap being adapted to cover a portion of the rear surface of the testing device;
a lancet having a first lock receiving region; and
at least one connection element having at least a first locking end, the first locking end adapted to interact within the first lock receiving region of the lancet to connect the connection element to the lancet.

Alternative Embodiment O

The reconfigurable integrated lancet system of Alternate Embodiment N wherein the connection element is integrally connected to the flexible lancet holding device frame.

Alternative Embodiment P

The reconfigurable integrated lancet system of Alternate Embodiment N wherein the flexible lancet holding device frame further has a sensor-pass through region adapted to allow a sensor to be placed within the testing device while the flexible lancet holding device frame is fastened to the testing device.

Alternative embodiment Q

The reconfigurable integrated lancet system of Alternate Embodiment N wherein the flexible lancet holding device frame further has a sensor-pass through region adapted to allow a sensor to be placed within the testing device while the flexible lancet holding device frame is fastened to the testing device.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A reconfigurable integrated testing system comprising:
a testing device having a housing;
a lancet holding device frame separate from the housing of the testing device and adapted to fasten to the housing of the testing device, the lancet holding device frame having a first lock receiving region, wherein when the lancet holding device frame is fastened to the housing of the testing device, the lancet holding device frame frames a periphery of the housing of the testing device and at least a portion of the housing of the testing device is disposed in the lancet holding device frame;
a lancet having a second lock receiving region; and
at least one connection mechanism having a first locking end and a second locking end, the first locking end adapted to interact within the first lock receiving region of the lancet holding device frame to connect the at least one connection mechanism to the lancet holding device frame, the second locking end adapted to interact within the second lock receiving region of the lancet to connect the at least one connection mechanism to the lancet.

2. The reconfigurable integrated testing system of claim 1, wherein the at least one connection mechanism is releasably connected to the lancet holding device frame.

3. The reconfigurable integrated testing system of claim 1, wherein the at least one connection mechanism is releasably connected to the lancet.

4. The reconfigurable integrated testing system of claim 1, wherein the at least one connection mechanism is fixedly connected to the lancet holding device frame.

5. The reconfigurable integrated testing system of claim 1, wherein the at least one connection mechanism is fixedly connected to the lancet.

6. The reconfigurable integrated testing system of claim 1, wherein the lancet holding device frame is a polymeric material.

7. The reconfigurable integrated testing system of claim 1, wherein the at least one connection mechanism is releasably connected to the lancet holding device frame and releasably connected to the lancet.

8. The reconfigurable integrated testing system of claim 1, wherein the first locking end of the at least one connection mechanism fits within the first lock receiving region of the lancet holding device frame.

9. The reconfigurable integrated testing system of claim 1, wherein the second locking end of the at least one connection mechanism fits within the second lock receiving region of the lancet.

10. The reconfigurable integrated testing system of claim 1, wherein the connection between the second locking end of the at least one connection mechanism and the second lock receiving region of the lancet is external to the lancet holding device frame.

* * * * *

UNITED STATES PATENT AND TRADEMARK OFFICE
CERTIFICATE OF CORRECTION

| | | |
|---|---|---|
| PATENT NO. | : 8,425,432 B2 | Page 1 of 1 |
| APPLICATION NO. | : 11/919835 | |
| DATED | : April 23, 2013 | |
| INVENTOR(S) | : Weiping Zhong | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1116 days.

Signed and Sealed this
Sixteenth Day of December, 2014

Michelle K. Lee
*Deputy Director of the United States Patent and Trademark Office*